(12) United States Patent
Lindsey et al.

(10) Patent No.: US 11,014,892 B2
(45) Date of Patent: May 25, 2021

(54) 5HT1F RECEPTOR AGONISTS AND MITOCHONDRIAL BIOGENESIS

(71) Applicants: MUSC FOUNDATION FOR RESEARCH DEVELOPMENT, Charleston, SC (US); The United States Government as Represented by the DEPARTMENT OF VETERANS AFFAIRS, Washington, DC (US)

(72) Inventors: Christopher C. Lindsey, Wadmalaw Island, SC (US); Craig C. Beeson, Charleston, SC (US); Yuri Karl Peterson, Charleston, SC (US); Rick G. Schnellmann, Tucson, AZ (US)

(73) Assignees: MUSC FOUNDATION FOR RESEARCH DEVELOPMENT, Charleston, SC (US); The United States Government as Represented by the DEPARTMENT OF VETERANS AFFAIRS, Washington, DC (US)

(*) Notice: Subject to any disclaimer, the term of this patent is extended or adjusted under 35 U.S.C. 154(b) by 0 days.

(21) Appl. No.: 16/347,163

(22) PCT Filed: Nov. 2, 2017

(86) PCT No.: PCT/US2017/059651
§ 371 (c)(1),
(2) Date: May 2, 2019

(87) PCT Pub. No.: WO2018/085491
PCT Pub. Date: May 11, 2018

(65) Prior Publication Data
US 2020/0055827 A1    Feb. 20, 2020

Related U.S. Application Data

(60) Provisional application No. 62/416,243, filed on Nov. 2, 2016.

(51) Int. Cl.
C07D 239/47   (2006.01)
A61P 13/12    (2006.01)
A61K 45/06    (2006.01)

(52) U.S. Cl.
CPC ............ *C07D 239/47* (2013.01); *A61P 13/12* (2018.01); *A61K 45/06* (2013.01)

(58) Field of Classification Search
CPC .................................................... C07D 239/47
See application file for complete search history.

(56) References Cited

U.S. PATENT DOCUMENTS

| 5,252,572 A | 10/1993 | Hermecz et al. |
| 5,962,474 A | 10/1999 | Audia et al. |
| 2012/0329820 A1 | 12/2012 | Cohen et al. |
| 2014/0024677 A1 | 1/2014 | Schnellmann et al. |

OTHER PUBLICATIONS

The International Search Report and Written Opinion, dated Jan. 17, 2018, in the corresponding PCT Appl. No. PCT/US2017/059651.
Pubchem-CID 25851674 Create Date: May 27, 2009 (May 27, 2009) pp. 1-9.
Pubchem-CID 65100318 Create Date: Oct. 23, 2012 (Oct. 23, 2012) pp. 1-9.
Pubchem-CID 86566752 Create Date: Jan. 20, 2015 (Jan. 20, 2015) pp. 1-8.
Garrett et al., "Agonism of the 5-Hydroxytryptamine 1F Receptor Promotes Mitochondrial Biogenesis and Recovery from Acute Kidney Injury", J Pharmacol Exp Ther., 2014, vol. 350, pp. 257-264.

*Primary Examiner* — Paul V Ward

(57) ABSTRACT

Provided herein are compounds of the formula (I): as well as pharmaceutically acceptable salts thereof, wherein the substituents are as those disclosed in the specification. These compounds, and the pharmaceutical compositions containing them, promote mitochondrial biogenesis and are useful for the treatment of, for example, acute kidney injury and chronic kidney disease.

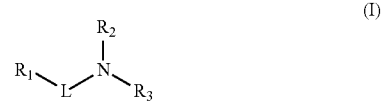

5 Claims, 1 Drawing Sheet

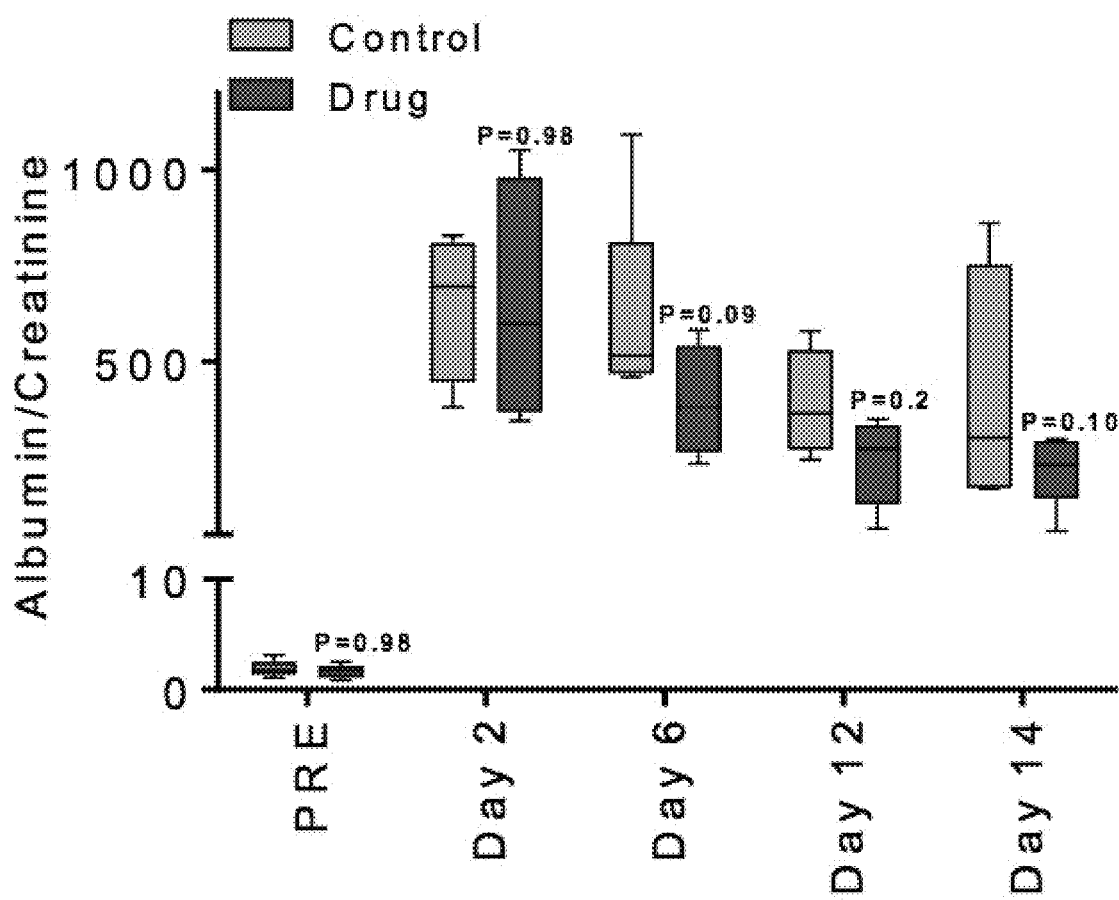

5HT1F RECEPTOR AGONISTS AND MITOCHONDRIAL BIOGENESIS

CROSS-REFERENCE TO RELATED APPLICATIONS

This application is a National Stage Application of PCT/US2017/059651 filed on Nov. 2, 2017, which claims priority from U.S. Provisional Patent Application No. 62/416,243 filed on Nov. 2, 2016. Each of prior mentioned applications is hereby expressly incorporated by reference herein in its entirety.

STATEMENT REGARDING FEDERALLY SPONSORED RESEARCH OR DEVELOPMENT

This invention was made with Government support under NIH grant 1R43DK103440. The Government has certain rights in the invention.

FIELD OF THE INVENTION

The invention is directed to compounds of formula (I):

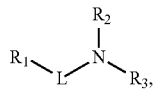
(I)

and to pharmaceutical compositions comprising the compounds. The compounds and compositions disclosed herein are 5HT1F receptor agonists, increase mitochondrial biogenesis and useful for the treatment of, for example, acute kidney injury and chronic kidney disease.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Currently, there is no approved therapeutic to treat acute kidney injury and the treatments for chronic kidney disease are inadequate. Kidney disease displays comorbidity with cardiovascular disease and diabetes, and is often linked to mitochondrial dysfunction[1-6]. For example, mitochondrial proteins and signaling mitochondrial biogenesis (MB) molecules are decreased within 24 h in a mouse model of acute kidney injury and do not recover over six days[7]. MB is the creation of new mitochondria and requires the tight coordination and production of nuclear encoded and mitochondrial encoded mitochondrial proteins and results in increased ATP generating capacity. While a number of MB signaling pathways have been reported, the number of chemicals reported to produce MB is limited.

The serotonin receptor family (5-HT receptors) consists of six GPCRs (5-$HT_{1-2,4-7}$) and one ligand-gated ion channel (5-$HT_3$). Serotonin receptors are typically thought to be located primarily in the central nervous system, but they are also found in platelets, cardiomyocytes, and renal cells[12-14].

It was previously reported that the 5-$HT_2$ receptor pan agonist DOI (1-(2,5-dimethoxy-4-iodophenyl)-2-aminopropane hydrochloride) is a potent inducer of MB in renal proximal tubular cells and accelerated the recovery of mitochondrial function following oxidant injury[12]. More recently, it was determined that two 5-$HT_{1F}$ receptor agonists, LY334370 (4-fluoro-N-[3-(1-methyl-4-piperidinyl)-1H-indol-5-yl]benzamide, CAS-182563-08-2) and LY344864 (N-[(3R)-3-(dimethylamino)-2,3,4,9-tetrahydro-1H-carbazol-6-yl]-4-fluorobenzamide, CAS-186544-26-3; 1-100 nM) increased maximal mitochondrial respiration, increased mitochondrial proteins [e.g., ATP synthase β, cytochrome c oxidase 1 (Cox1), and NADH dehydrogenase (ubiquinone) 1β subcomplex subunit 8 (NDUFB8)] in RPTC[8]. Small interfering RNA knockdown of the 5-HT1F receptor blocked agonist-induced MB[8]. Furthermore, LY344864 increased peroxisome proliferator-activated receptor coactivator 1-α, Cox1, and NDUFB8 transcript levels and mitochondrial DNA (mtDNA) copy number in murine renal cortex, heart, and liver[8]. Finally, LY344864 accelerated recovery of renal function, as indicated by decreased blood urea nitrogen (BUN), kidney injury molecule 1 (KIM-1) and increased mtDNA copy number following ischemia/reperfusion-induced AKI[8]. In summary, these studies revealed that the 5-$HT_{1F}$ receptor is linked to MB, 5-$HT_{1F}$ receptor agonism promotes MB in vitro and in vivo, and 5-$HT_{1F}$ receptor agonism promotes recovery from AKI injury.

A need exists in the art, therefore, for new 5-$HT_{1F}$ receptor agonists that induce MB and are useful for the treatment of AKI.

SUMMARY OF THE INVENTION

The present invention is directed to a compound according to formula (I):

(I)

wherein:
L is a bond, —C(O)—, —C(O)$CH_2$— or —S(O)$_2$—;
$R_1$ is an aryl group, a heteroaryl group or an 8- to 10-membered bicyclic heteroaryl group, said aryl, heteroaryl and 8- to 10-membered bicyclic heteroaryl groups optionally mono-, bi- or tri-substituted independently with hydrogen, alkoxy, (=O), —NH-alkoxy, —$NH_2$, —OH, halogen, lower alkyl, —NHC(O)N($CH_3$)$_2$, —NHS(O)$_2$-phenyl or —NHC(O)-phenyl;
$R_2$ and $R_3$ are, independently of each other, hydrogen, lower alkyl, alkoxy, —NH-lower alkyl, heteroaryl, —S(O)$_2$-phenyl or indolinyl, said heteroaryl and indolinyl groups optionally substituted independently with lower alkyl, C(O)-alkoxy or —C(O)$R_4$,
or $R_2$ and $R_3$, together with the nitrogen atom to which they are attached, combine to form a six-membered heterocycloalkyl group optionally substituted with lower alkyl; and
$R_4$ is a heterocycloalkyl group optionally substituted with lower alkyl,
or a pharmaceutically acceptable salt thereof, with the proviso that said compound is not 2,4,6-trifluoro-N-(6-(1-methylpiperidine-4-carbonyl)pyridin-2-yl)benzamide.

The present invention is also directed to pharmaceutical compositions containing the compounds of formula (I) and to methods of using these compounds.

BRIEF DESCRIPTION OF THE DRAWINGS

FIG. 1 is a graph showing that the compound of Example 6 (2,4,6-trifluoro-N-(6-(4-methylpiperazine-1-carbonyl)pyridin-2-yl)benzamide) attenuates albuminuria in a murine model of glomerular disease.

DETAILED DESCRIPTION OF THE INVENTION

Provided herein are novel 5-$HT_{1F}$ receptor agonists that induce MB and are useful for the treatment of AKI and chronic kidney disease. It is to be understood that the descriptions of the present invention have been simplified to illustrate elements that are relevant for a clear understanding of the present invention, while eliminating, for the purpose of clarity, many other elements found in typical pharmaceutical compositions. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

As used herein, the term "alkenyl", alone or in combination with other groups, refers to a straight-chain or branched hydrocarbon residue having an olefinic bond.

As used herein, the term "alkyl", alone or in combination with other groups, refers to a branched or straight-chain monovalent saturated aliphatic hydrocarbon radical of one to twenty carbon atoms, in one embodiment one to sixteen carbon atoms, in another embodiment one to ten carbon atoms.

The term "lower alkyl", alone or in combination with other groups, refers to a branched or straight-chain alkyl radical of one to nine carbon atoms, in one embodiment one to six carbon atoms, in another embodiment one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

As used herein, the term "alkoxy" means alkyl-O—. Alkoxy substituent groups or alkoxy-containing substituent groups may be substituted by, for example, one or more alkyl or halo groups.

As used herein, the term "halogen" means a fluorine, chlorine, bromine or iodine radical.

The term "aryl" refers to an aromatic mono- or polycarbocyclic (e.g., bicyclic) radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The term "heteroaryl," refers to an aromatic mono- or polycyclic (e.g., bicyclic) radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic (e.g., bicyclic) alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate.

The alkyl, lower alkyl, aryl, heteroaryl, cycloalkyl and heterocycloalkyl groups may be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, in one embodiment, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. In certain embodiments, fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Certain embodiments, water, saline, aqueous dextrose, and glycols are liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 10,000 mg per day. In one embodiment, the therapeutically effective amount is in an amount of from about 5 mg to about 10,000 mg per day. In another embodiment, the dose of a compound of the present invention is in the range of about 1 to about 1,000 mg per day. In another embodiment, the therapeutically effective amount is in an amount of from about 1 mg to about 500 mg per day. In a further embodiment, one to four doses can be given per day.

It will be appreciated, that the compounds of general formula I of this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. For example, the compounds of formula I can be prepared according to the following schemes:

Scheme 1

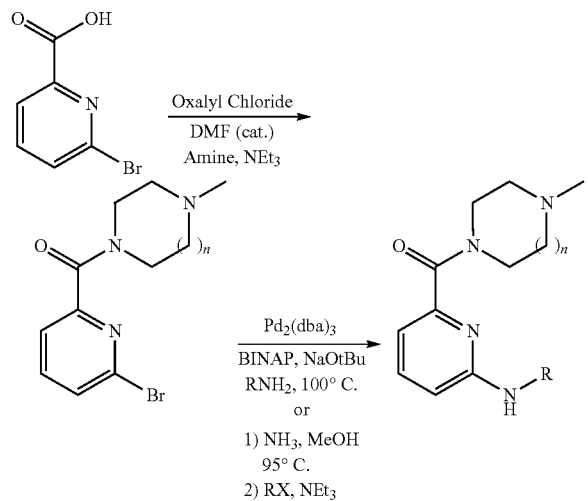

As shown in Scheme 1 above, R can be 2,4,6-trifluorobenzoyl, phenylsulfonyl, tolusulfonyl, benzoyl, benzimidazole, benzoxazole, benzothiazole, N,N-dimethylurea, phenyl carbonyl, aryl carbonyl, heteroaryl carbonyl, halo-heteroaryl carbonyl, pyridine carbonyl, phenyl boronate, aryl hydroxy boron, heteroaryl boronate, halo-benzoyl, dihalobenzoyl, trihalo-benzoyl, phenyl hydroxy boron, N,N,-dimethyl urea, methyl urea, alkyl urea, aryl urea, N,N,-dimethyl sulfamate, methyl sulfamate, alkyl sulfamate, dialkyl sulfamate, aryl sulfamate, di aryl sulfamate, 3-dimethyl amino cyclobut-3-ene-1,2-dione, or di-alkyl amino cyclobut-3-ene, 1,2-dione. X can be a halide, chlorine, bromine, carbonyl-imidazole, tosylate, carbonate, sulfur alkyl ether, or mesylate As shown in Scheme 2 above, R1 can be benzoyl, 2,4,6-trifluorobenzoyl, 2-fluoro-benzoyl, difluorobenzoyl, bromobenzoyl, phenylsulfonyl, toluenesulfonyl, pyridinecarbonyl, benzoxazole, phenyl carbonyl, aryl carbonyl, heteroaryl carbonyl, halo-heteroaryl carbonyl, pyridine carbonyl, phenyl boronate, aryl hydroxy boron, heteroaryl boronate, halo-benzoyl, dihalobenzoyl, trihalo-benzoyl, phenyl hydroxy boron, benzimidazole, N,N,-dimethyl urea, methyl urea, alkyl urea, aryl urea, N,N,-dimethyl sulfamate, methyl sulfamate, alkyl sulfamate, dialkyl sulfamate, aryl sulfamate, di aryl sulfamate, 3-dimethyl amino cyclobut-3-ene-1,2-dione, or di-alkyl amino cyclobut-3-ene, 1,2-dione. R6 can be benzoyl, 2,4,6-trifluorobenzoyl, 2-fluoro-benzoyl, phenylsulfonyl, toluenesulfonyl, bromobenzoyl, pyridinecarbonyl, benzoxazole, benzimidazole, phenyl carbonyl, aryl carbonyl, heteroaryl carbonyl, halo-heteroaryl carbonyl, pyridine carbonyl, phenyl boronate, aryl hydroxy boron, heteroaryl boronate, halo-benzoyl, dihalobenzoyl, trihalo-benzoyl, or phenyl hydroxy boron. X can be a halide, chlorine, bromine, carbonyl-imidazole, tosylate, carbonate, sulfur alkyl ether, or mesylate.

Scheme 3

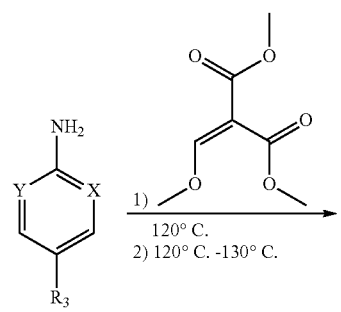

Scheme 2

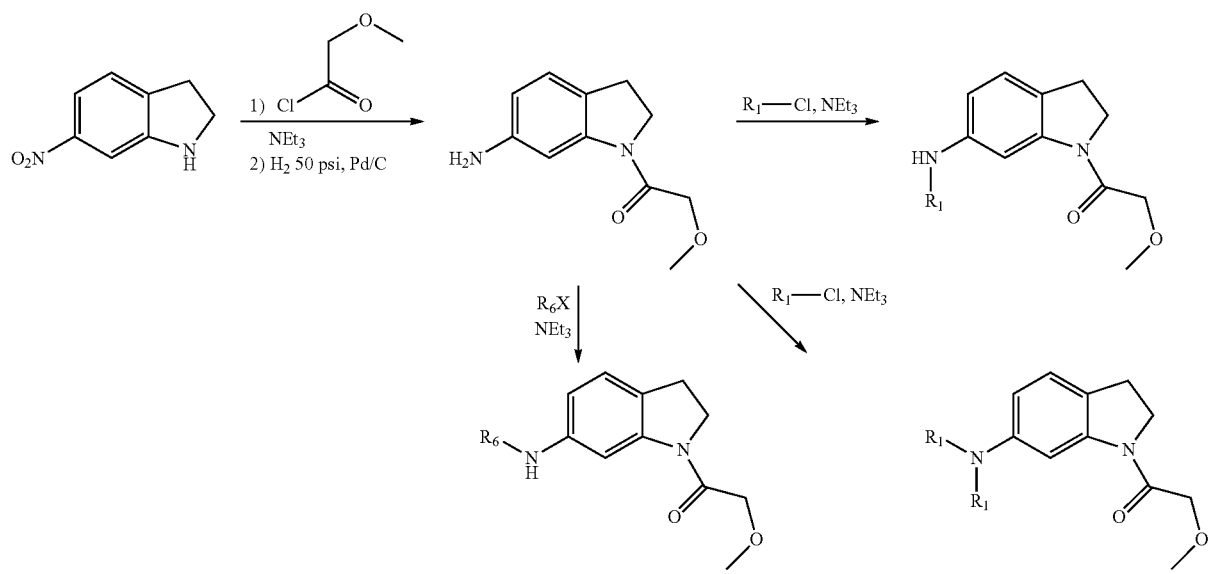

-continued

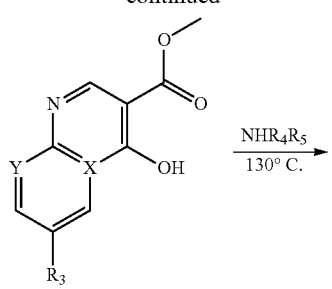

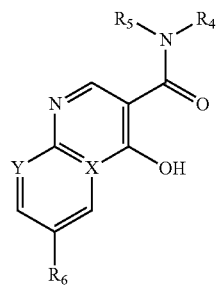

As shown in Scheme 3 above, R3 can be hydrogen, methoxy, ethoxy, alkyl ether, amine, mono alkyl amine, or dialkyl amine, R4 can be hydrogen, methoxyethyl, alkoxy ethyl, or N-methylpiperazine, R5 can be hydrogen, alkyl, methoxyethyl, mono-alkyl amino ethyl, di-alkyl amino ethyl, mono substituted alkyl amine, di-substituted alkyl amine, alkoxy, morpholine. N-methylpiperazine, or alkaloid, and R6 can be hydrogen, alkyl, methoxyethyl, alkoxy ethyl, mono-alkyl amino ethyl, di-alkyl amino ethyl, mono substituted alkyl amine, di-substituted alkyl amine, alkoxy, morpholine. N-methylpiperazine, or alkaloid. Y can be CH, N, or C—OMe. X can be C or N.

Scheme 4

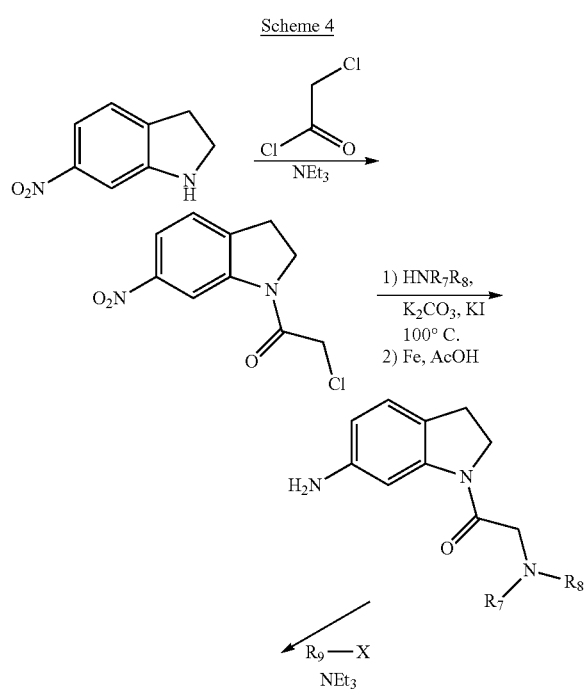

-continued

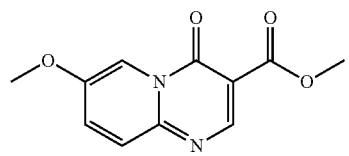

As shown in Scheme 4 above, R7 can be methyl or ethyl, alkyl, methoxy ethyl, alkoxy ethyl, alkoxy propyl, morpholine, piperazine or alkaloid, R8 can be methyl, ethyl, alkyl, morpholine, piperazine, or alkaloid, R9 can be benzoyl, 2,4,6-trifluorobenzoyl, 2-fluoro-benzoyl, difluorobenzoyl, bromobenzoyl, phenylsulfonyl, toluenesulfonyl, alkylsulfonyl, pyridinecarbonyl, heteroaryl carbonyl, benzoxazole, benzimidazole, aryl, phenyl, substituted phenyl, hetero aryl, N,N,-dimethyl urea, methyl urea, alkyl urea, aryl urea, N,N,-dimethyl sulfamate, methyl sulfamate, alkyl sulfamate, dialkyl sulfamate, aryl sulfamate, di aryl sulfamate, 3-dimethyl amino cyclobut-3-ene-1,2-dione, or di-alkyl amino cyclobut-3-ene, 1,2-dione. X can be a halide, chlorine, bromine, carbonyl-imidazole, tosylate, carbonate, or mesylate.

The invention will now be further described in the Examples below, which are intended as an illustration only and do not limit the scope of the invention.

EXAMPLES

All reagents and chemical solvents were used from commercially available sources without further purification. All materials, solvents, and chemical reagents were purchased from Fisher Scientific.

I. Preparation of Representative Intermediates of the Invention

Methyl 7-methoxy-4-oxo-4H-pyrido[1,2-a]pyrimidine-3-carboxylate

To an oven dried flask equipped with a stir bar and air-to-air condenser was added 5-methoxypyridin-2-amine (0.2 grams, 1.61 mmol) and dimethyl 2-(methoxymethylene)malonate (0.281 grams, 1.61 mmol). The mixture was heated to 130° C. for three hours then cooled to room temperature. The solid material collected by filtration, washed with hexanes, and used without further purification.

To a flask charged with the dimethyl 2-(((5-methoxypyridin-2-yl)amino)methylene)malonate (1.61 mmol) was added diphenyl ether (4.0 mL). The solution was heated to 250° C. for 24 hours, then cooled to room temperature. The desired material precipitated upon the addition of hexanes and collected by filtration. The material was then used without further purification. Calculated mass for Chemical Formula: $C_{11}H_{10}N_2O_4$ Exact Mass: 234.06 observed 235.1 (M+1, MM API/ESI).

Methyl 7-methoxy-4-oxo-4H-pyrimido[1,2-a]pyrimidine-3-carboxylate

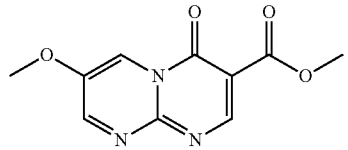

To an oven dried flask equipped with a stir bar and air-to-air condenser was added 5-methoxypyrimidin-2-amine (0.2 grams, 1.6 mmol) and 2-(methoxymethylene)malonate (0.2784 grams, 1.6 mmol). The mixture was heated to 130° C. for five hours then cooled to room temperature. The solid material collected by filtration, washed with hexanes, and used without further purification.

To an oven dried flask equipped with a stir bar and air-to-air condenser was added dimethyl 2-(((5-methoxypyrimidin-2-yl)amino)methylene)malonate (1.6 mmol) and 4.0 mL of diphenyl ether. The solution was heated to 250° C. for 24 hours. It was then cooled to room temperature. The crude material was precipitated using hexanes and collected by filtration. Purification was done using a Teledyne ISCO using a reverse phase C18 column, water with 0.1% formic acid/acetonitrile gradient. This afforded the desired intermediate, 95.0 mg. Calculated mass for Chemical Formula: $C_{10}H_9N_3O_4$ Exact Mass: 235.06 observed 236.1 (M+1, MM API/ESI).

Methyl 4-hydroxy-6,8-dimethoxyquinoline-3-carboxylate

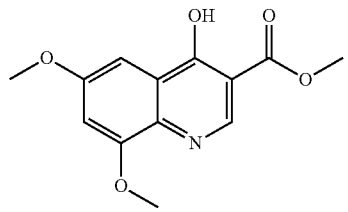

To an oven dried flask equipped with a stir bar and air-to-air condenser was added 2,4-dimethoxyaniline (1.05 grams, 13.7 mmol) and 2-(methoxymethylene)malonate (2.387 grams, 13.7 mmol). The mixture was heated to 120° C. for four hours then cooled to room temperature. The solid material collected by filtration, washed with hexanes, and used without further purification.

To a flask charged with dimethyl 2-(((2,4-dimethoxyphenyl)amino)methylene)malonate (13.7 mmol) was added Eaton's reagent (13.7 mL). The solution was heated to 100° C. for 4 hours, then cooled to room temperature. It was then carefully poured into a solution of $NaHCO_3$ (sat.) to afford a precipitate. The precipitate was collected by filtration and used without further purification. Calculated mass for Chemical Formula: $C_{13}H_{13}NO_5$ Exact Mass: 263.08 observed 264.1 (M+1, MM API/ESI).

(6-Bromopyridin-2-yl)(4-methylpiperazin-1-yl)methanone

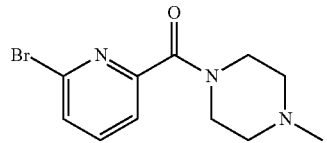 [SMILES: CN1CCN(C(=O)c2cccc(Br)n2)CC1]

To an oven dried flask equipped with a stir bar was added 6-bromo-picolinic acid (1.0 gram, 4.95 mmol, 0.3 M in anhydrous dichloromethane). While stirring at room temperature, oxalyl chloride (0.54 mL, 6.43 mmol) was added followed by 18 uL of anhydrous DMF. The reaction continued to stir for 60 minutes. It was then concentrated using a rotary evaporator. The residue was then taken up in 16 mL anhydrous dichloromethane. While stirring at 0° C., 1-methylpiperazine (0.61 mL, 5.4 mmol) was added followed by treiethylamine (0.88 mL, 6.4 mmol). The stirring solution was slowly allowed to warm to room temperature overnight. The reaction was then quenched upon the addition was water. The organic material was then extracted using dichloromethane. The aqueous material was washed with dichloromethane twice. The combined organic material was washed with $NaHCO_3$ (sat.), brine, dried with Na2SO4, filtered and concentrated. Purification was done using a Teledyne ISCO on a silica support using a dichloromethane/methanol gradient. This afforded the desired material, 1.0 grams. Calculated mass for Chemical Formula: $C_{11}H_{14}BrN_3O$ Exact Mass: 283.03 observed 284.0 (M+1, MM API/ESI).

2,4,6-Trifluorobenzamide

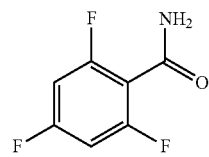

To an oven dried flask equipped with a stir bar cooled under argon, was added NH3 (3.27 mL, 7.0 N in methanol). After cooling the stirred solution to 0° C., 2,4,6-trifluorobenzoyl chloride (0.5 mL, 3.81 mmol) was added dropwise, and the solution stirred overnight, slowly warming up to room temperature. It was then cooled to 0° C. Once a precipitate had formed, it was collected by filtration. The precipitate was rinsed with cold methanol. This afforded the desired product which was used without further purification. Calculated mass for Chemical Formula: $C_7H_4F_3NO$ Exact Mass: 175.02 observed 176.1 (M+1, MM API/ESI).

1-(6-Aminoindolin-1-yl)-2-methoxyethan-1-one

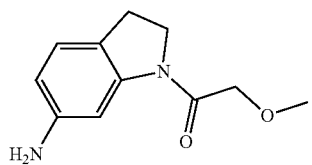

To an oven dried flask equipped with a stir bar cooled under argon was added 6-nitroindoline (2.0 grams, 12.2 mmol) and 61.0 mL of anhydrous drichloromethane. While stirring at 0° C. 2-methoxyacetyl chloride (1.3 mL, 14.6 mmol) was added followed by triethylamine (2.2 mL, 16 mmol). The reaction slowly warmed to room temperature. Once complete, determined by LCMS, the reaction was quenched with water, and the organic material extracted using dichloromethane. The aqueous material was washed with dichloromethane twice. The combined organic material was washed with NaHCO$_3$ (sat.), brine, dried with Na2SO4, filtered and concentrated. The crude material was then used without further purification.

To a Parr Bomb shaker flask charged with the crude 2-methoxy-1-(6-nitroindolin-1-yl)ethan-1-one (0.5 grams, in 50 mL methanol) was added 0.2 grams Pd/C (10% wet). The solution was then exposed to a hydrogen atmosphere (60 psi) and shaken over night at this pressure. The next day once the hydrogen atmosphere was removed, the solution was filtered through a celite plug and rinsed with methanol. The organic solution was concentrated to afford 0.225 grams of desired material that was used without further purification. Calculated mass for Chemical Formula: $C_{11}H_{14}N_2O_2$ Exact Mass: 206.11 observed 207.1 (M+1, MM API/ESI).

2-(Methylthio)benzo[d]oxazole

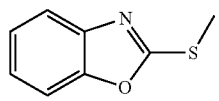

To an oven dried flask equipped with a stir bar cooled under argon was added benzo[d]oxazole-2(3H)-thione (0.375 grams, 2.48 mmol) and K2CO3 (1.37, 9.92 mmol). The was taken up in 20.0 mL anhydrous acetone. After stirring for approximately minutes at room temperature, methyl iodide (0.25 mL, 3.97 mmol) was added. The solution continued to stir at room temperature overnight. The next day the solution was filtered through a plug of celite, and rinsed with dichloromethane and ethyl acetate. The solution was then concentrated. It was then taken up in ethyl acetate, filtered, and concentrated again. It was then used without further purification. Calculated mass for Chemical Formula: $C_8H_7NOS$ Exact Mass: 165.02 observed 166.1 (M+1, MM API/ESI).

2-chloro-1-(6-nitroindolin-1-yl)ethan-1-one

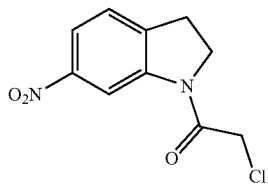 [SMILES: O=C(CCl)N1CCc2ccc([N+](=O)[O-])cc21]

To an oven dried flask equipped with a stir bar cooled under an inert atmosphere was added 6-nitroindoline (1.0 grams, 6.10 mmol, 0.3 M in anhydrous dichloromethane). While stirring at room temperature triethylamine (1.7 mL, 12.2 mmol) was added followed by chloroacetylchloride (0.63 mL, 7.9 mmol). The reaction stirred overnight. The next day the reaction was diluted with water and extracted using chloroform. The aqueous layer was washed with chloroform twice more. The combined organic material was washed with brine, dried with Na2SO4, filtered, and concentrated. It was then used without any further purification. (1.39 grams collected). Calculated mass for $C_{10}H_9ClN_2O_3$, 240.03, observed mass, 241.0 (M+1, Cl).

2-(dimethylamino)-1-(6-nitroindolin-1-yl)ethan-1-one

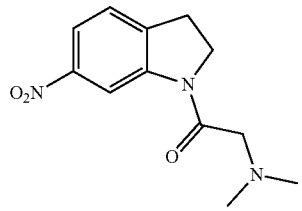

To an oven dried flask equipped with a stir bar cooled under an inert atmosphere was added 2-chloro-1-(6-nitroindolin-1-yl)ethan-1-one (0.2 grams, 0.83 mmol), potassium iodide (12.0 mg, 0.08 mmol), and $K_2CO_3$ (0.221 grams, 1.6 mmol). The mixture was taken up in 5.0 mL of anhydrous DMF. Dimethylamine (0.12 mL, 1.08 mmol, 40% in water) was then added. The mixture was heated in a Biotage microwave to 100° C. for 12 hours. The reaction was then concentrated. The slurry was taken up in chloroform, filtered, and concentrated. The crude material was used without any further purification. Calculated mass for $C_{12}H_{15}N_3O_3$, 249.11, observed mass, 250.1 (M+1, MM).

1-(6-aminoindolin-1-yl)-2-(dimethylamino)ethan-1-one

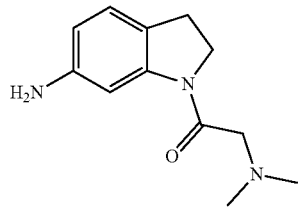 [SMILES: CN(C)CC(=O)N1CCc2ccc([N+](=O)[O-])cc21]

To an oven dried flask equipped with a stir bar cooled under an inert atmosphere was added 2-(dimethylamino)-1-(6-nitroindolin-1-yl)ethan-1-one (0.83 mmol), 1.6 mL glacial acetic acid, 0.5 mL water. While stirring vigorously, iron (0.137 grams, 2.49 mmol) was added. After thirty minutes of continued vigorous stirring, iron (0.137 grams, 2.49 mmol) was added. After thirty minutes of continued vigorous stirring, iron (0.137 grams, 2.49 mmol) was added. The solution was then diluted with methanol and celite, and filtered through celite plug. The plug was then rinsed with methanol washes until no color was observed passing through the filter. The solution was then concentrated. Calculated mass for $C_{12}H_{17}N_3O$, 219.14, observed mass, 220.2 (M+1, MM).

II. Preparation of Representative Compounds of the Invention

Example 1

7-methoxy-N-(2-methoxyethyl)-4-oxo-4H-pyrido[1,2-a]pyrimidine-3-carboxamide

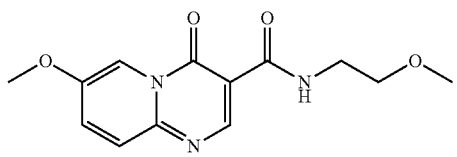

To a Biotage microwave vial (0.5 mL-2.0 mL) that was stored in an oven at 150° C. for at least 1.5 hours and cooled under argon, was added methyl 7-methoxy-4-oxo-4H-pyrido[1,2-a]pyrimidine-3-carboxylate (0.03 grams, 0.128 mmol) followed by 0.6 mL of 2-methoxy-ethylamine. The solution was heated in the microwave to 130° C. for 12 hours. The solution was then concentrated using a rotary evaporator. It was then diluted with 3.0 mL of water and 1.0 mL of methanol. The solution was then concentrated. Purification was done using a Teledyne ISCO using a reverse phase C18 column, water with 0.1% formic acid/acetonitrile gradient. The desired material was further purified using a Teledyne ISCO on silica support using a gradient of dichloromethane and 8/2 dichoromethane-methanol with 0.1% NH$_4$OH. This afforded the desired product, 3.0 mg. 1H-NMR (CD3OD) d 9.03, 8.75 (d, 1H), 7.92 (dd, 1H), 7.79 (d, 1H), 4.03 (s, 3H), 3.61 (m, 4H), 3.41 (s, 3H). Calculated mass for Chemical Formula: C$_{13}$H$_{15}$N$_3$O$_4$ Exact Mass: 277.11 observed 278.1 (M+1, MM API/ESI).

Example 2

N-(2-methoxyethyl)-7-((2-methoxyethyl)amino)-4-oxo-4H-pyrido[1,2-a]pyrimidine-3-carboxamide

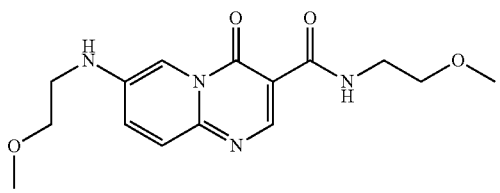 [SMILES: COCCNC(=O)c1cnc2ccc(NCCOC)cn2c1=O]

This product was made in a similar way to 7-methoxy-N-(2-methoxyethyl)-4-oxo-4H-pyrido[1,2-a]pyrimidine-3-carboxamide. 1H-NMR (CD3OD) d 8.92 (d, 1H), 8.34 (d, 1H), 7.77 (dd, 1H), 7.65 (dd, 1H), 3.68 (t, 2H), 3.64-3.58 (m, 6H), 3.41 (s, 3H), 3.41 (s, 3H), 3.39 (t, 2H). Calculated mass for Chemical Formula: C$_{15}$H$_{20}$N$_4$O$_4$ Exact Mass: 320.15 observed 321.2 (M+1, MM API/ESI).

Example 3

2-amino-N,1-bis(2-methoxyethyl)-6-oxo-1,6-dihydropyrimidine-5-carboxamide

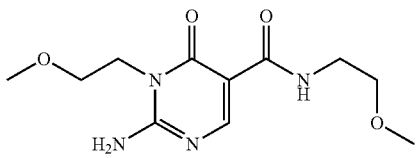

To a flask charged with methyl 7-methoxy-4-oxo-4H-pyrimido[1,2-a]pyrimidine-3-carboxylate 0.034 grams, 0.14 mmol) was added 0.6 mL of 2-methoxy-ethylamine. The solution was then heated using a Biotage Initiator at 130° C. for 12 hours. The reaction was then concentrated, diluted with 3 mL of water and 1.0 mL of methanol. Once concentrated again, the residue was purified using a Teledyne ISCO using a reverse phase C18 column, water with 0.1% formic acid/acetonitrile gradient. This afford the desired compound, 3.5 mg. 1H-NMR (CD3OD) d 8.53 (s, 1H), 3.59-3.54 (m, 4H), 3.53 (s, 3H), 3.39-3.30 (m, 7H). Calculated mass for Chemical Formula: C$_{11}$H$_{18}$N$_4$O$_4$ Exact Mass: 270.13 observed 271.2 (M+1, MM API/ESI).

Example 4

4-hydroxy-6,8-dimethoxy-N-(2-methoxyethyl)quinoline-3-carboxamide

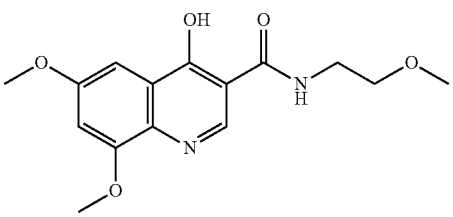

To an oven dried flask cooled to room temperature under argon was added methyl 6,8-dimethoxy-4-oxo-1,4-dihydroquinoline-3-carboxylate (0.2 grams, 0.76 mmol). It was then taken up in 2-methoxy-ethylamine (1.9 mL) and heated using a Biotage microwave initiator to 130° C. for 12 hours. The solution was then concentrated. Purification was done using a Teledyne ISCO using a reverse phase C18 column, water with 0.1% formic acid/acetonitrile gradient. This afforded the desired product, 46.8.0 mg. 1H-NMR (CD3OD) d 8.62 (s, 1H), 7.26 (d, 1H), 6.90 (d, 1H), 4.04 (s, 3H), 3.90 (s, 3H), 3.60 (m, 4H), 3.41 (s, 3H). Calculated mass for Chemical Formula: C$_{15}$H$_{18}$N$_2$O$_5$ Exact Mass: 306.12, observed 307.1 (M+1, MM API/ESI).

Example 5

(4-hydroxy-6,8-dimethoxyquinolin-3-yl)(4-methylpiperazin-1-yl)methanone

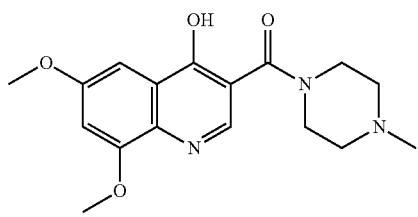

The title compound was prepared in a similar way to 4-hydroxy-6,8-dimethoxy-N-(2-methoxyethyl)quinoline-3-carboxamide using 1-methyl piperazine. 1H-NMR (CD3OD) d 8.01 (s, 1H), 7.25 (d, 1H), 6.93 (d, 1H), 4.04 (s, 3H), 3.90 (s, 3H), 3.89 (s, 2H), 3.51 (s, 2H), 2.81 (s, 4H), 2.54 (s, 3H). Calculated mass for Chemical Formula: $C_{17}H_{21}N_3O_4$ Exact Mass: 331.15, observed 332.2 (M+1, MM API/ESI).

Example 6

2,4,6-trifluoro-N-(6-(4-methylpiperazine-1-carbonyl)pyridin-2-yl)benzamide

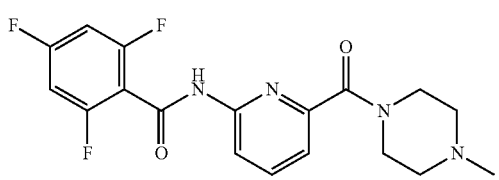 [SMILES: CN1CCN(C(=O)c2cccc(NC(=O)c3c(F)cc(F)cc3F)n2)CC1]

To an oven dried flask equipped with a stir bar, cooled under argon was added (6-bromopyridin-2-yl)(4-methylpiperazin-1-yl)methanone (0.142 grams, 0.5 mmol), 2,4,6-trifluorobenzamide (0.105 grams, 0.6 mmol), sodium t-butoxide (0.0673 grams, 0.7 mmol) and 5.0 mL of anhydrous toluene. After sparging with argon for 40 minutes, Pd2dba3 (0.092 grams, 0.01 mmol) and +/−BINAP (0.012 grams, 0.04 mmol) was added. The vessel was then sealed and heated to 95° C., stirring overnight. The next day, the reaction was filtered through a 45 micron frit, and concentrated. Purification was done using a Teledyne ISCO on a silica support using dichloromethane/dichloromethane methanol containing NH3 (2.0M). Further purification was done using a Teledyne ISCO using a reverse phase C18 column, water with 0.1% formic acid/acetonitrile gradient. This afforded the desired product, 46.8 mg. 1H-NMR (CD3OD) d 8.25 (d, 1H), 7.99 (m, 1H) 7.47 (d, 1H), 7.03 (m, 2H) 3.92-3.82 (m, 4H), 2.98 (m, 4H), 2.65 (bs, 3H). Calculated mass for Chemical Formula: $C_{18}H_{17}F_3N_4O_2$ Exact Mass: 378.13, observed 379.1 (M+1, MM API/ESI).

Example 7

2,4,6-trifluoro-N-(6-(4-methyl-1,4-diazepane-1-carbonyl)pyridin-2-yl)benzamide

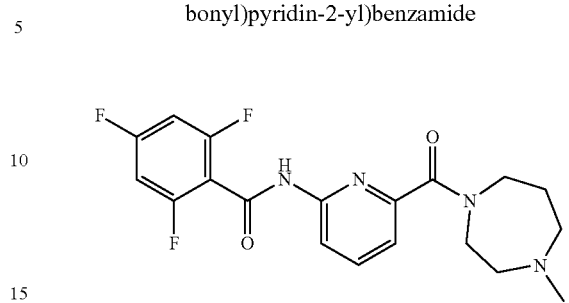

The title compound was prepared in a similar manner to 2,4,6-trifluoro-N-(6-(4-methylpiperazine-1-carbonyl)pyridin-2-yl)benzamide. 1H-NMR (CD3OD) d 8.25 (dd, 1H), 8.01 (dd, 1H) 7.48 (dd, 1H), 7.04 (m, 2H) 3.94 (bs, 1H), 3.80 (m, 2H), 3.67 (t, 1H), 3.33 (m, 2H), 2.83 (m, 4H), 2.20 (m, 3H). Calculated mass for Chemical Formula: $C_{19}H_{19}F_3N_4O_2$ Exact Mass: 392.15, observed 393.1 (M+1, MM API/ESI).

Example 8

4-methyl-N-(6-(4-methylpiperazine-1-carbonyl)pyridin-2-yl)benzenesulfonamide

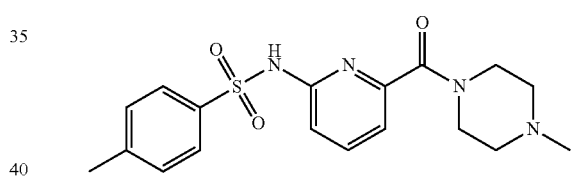

The title compound was prepared in a similar manner to 2,4,6-trifluoro-N-(6-(4-methylpiperazine-1-carbonyl)pyridin-2-yl)benzamide. 1H-NMR (CD3OD) d 7.83 (d, 2H), 7.77 (dd, 1H), 7.32 (d, 2H), 7.19 (m, 2H), 3.76 (s, 2H), 3.45 (s, 2H), 2.58 (s, 2H), 2.44 (s, 2H), 2.37 (m, 6H). Calculated mass for Chemical Formula: $C_{18}H_{22}N_4O_3S$ Exact Mass: 374.14 observed 375.2 (M+1, MM API/ESI).

Example 9

1,1-dimethyl-3-(6-(4-methylpiperazine-1-carbonyl)pyridin-2-yl)urea

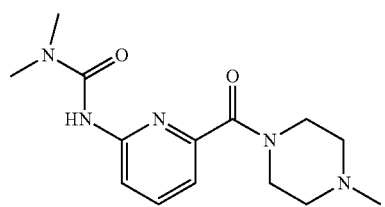

The title compound was prepared in a similar manner to 2,4,6-trifluoro-N-(6-(4-methylpiperazine-1-carbonyl)pyridin-2-yl)benzamide. 1H-NMR (CD3OD) d 7.85 (dd, 1H), 7.88 (dd, 1H), 7.81 (dd, 1H), 7.17 (dd, 1H), 3.77 (m, 2H), 3.54 (m, 2H), 3.05 (s, 6H), 2.57 (s, 2H), 2.48 (s, 2H), 2.36 (s, 3H). Calculated mass for Chemical Formula: $C_{14}H_{21}N_5O_2$, Exact Mass: 291.17, observed 292.2 (M+1, MM API/ESI).

Example 10

(6-((1H-benzo[d]imidazol-2-yl)amino)pyridin-2-yl)(4-methylpiperazin-1-yl)methanone

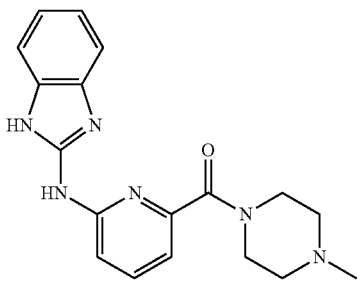 [SMILES: CN1CCN(C(=O)c2cccc(Nc3nc4ccccc4[nH]3)n2)CC1]

The title compound was prepared in a similar manner to 2,4,6-trifluoro-N-(6-(4-methylpiperazine-1-carbonyl)pyridin-2-yl)benzamide. 1H-NMR (CD3OD) d 7.85 (dd, 1H), 7.45 (m, 2H), 7.18 (d, 1H), 7.13 (m, 3H), 3.87 (m, 2H), 3.53 (m, 2H), 2.62 (s, 2H), 2.46 (s, 2H), 2.34 (s, 3H). Calculated mass for Chemical Formula: $C_{18}H_{20}N_6O$ Exact Mass: 336.17, observed 337.2 (M+1, MM API/ESI).

Example 11

N-(6-(4-methylpiperazine-1-carbonyl)pyridin-2-yl)benzamide

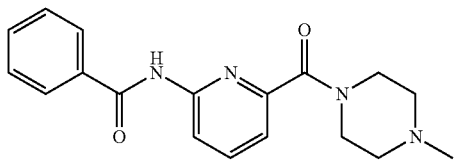 [SMILES: CN1CCN(C(=O)c2cccc(NC(=O)c3ccccc3)n2)CC1]

The title compound was prepared in a similar manner to 2,4,6-trifluoro-N-(6-(4-methylpiperazine-1-carbonyl)pyridin-2-yl)benzamide. 1H-NMR (CD3OD) d 8.8.34 (d, 1H), 7.99-7.94 (m 3H), 7.63-7.51 (m, 3H), 7.33, (d 1H), 3.80, (s, 2H), 3.58 (s, 2H), 2.56 (s, 2H), 2.48 (s, 2H), 2.34 (s, 3H). Calculated mass for Chemical Formula: Chemical Formula: $C_{18}H_{20}N_4O_2$ Exact Mass: 324.16, observed 325.2 (M+1, MM API/ESI).

Example 12

1-(6-(benzo[d]oxazol-2-ylamino)indolin-1-yl)-2-methoxyethan-1-one

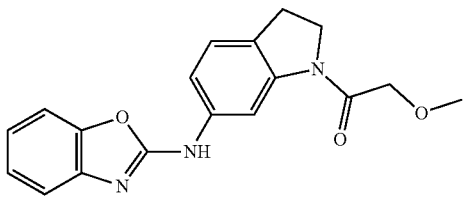 [SMILES: COCC(=O)N1CCc2ccc(Nc3nc4ccccc4o3)cc21]

To a flask charged with 1-(6-aminoindolin-1-yl)-2-methoxyethan-1-one (0.02 grams, 0.09 mmol) was added 2-(methylthio)benzo[d]oxazole (0.024 grams, 0.15 mmol) was added ethanol (0.6 mL). The solution was heated using a biotage microwave initiator to 140° C. for 8 hours. Purification was done using a Teledyne ISCO using a reverse phase C18 column, water with 0.1% formic acid/acetonitrile gradient. This afforded the desired product, 5.0 mg. 1H-NMR (CD3OD) d 8.40 (s, 1H), 7.49 (d, 1H), 7.37 (m, 2H), 7.23 (m, 2H), 7.11 (dd, 1H), 5.24 (s, 2H), 4.09 (m, 2H), 3.49 (s, 3H), 3.20 (m, 2H). Calculated mass for Chemical Formula: Chemical Formula: $C_{18}H_{17}N_3O_3$ Exact Mass: 323.13, observed 324.1 (M+1, MM API/ESI).

Example 13

2,4-difluoro-N-(1-(2-methoxyacetyl)indolin-6-yl)benzamide

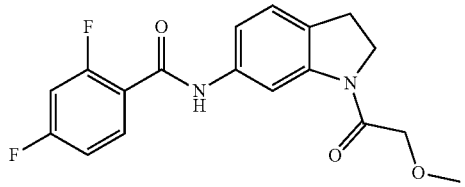 [SMILES: COCC(=O)N1CCc2ccc(NC(=O)c3ccc(F)cc3F)cc21]

To an oven dried flask equipped with a stir bar, cooled under argon was added 1-(6-aminoindolin-1-yl)-2-methoxyethan-1-one (0.02 grams, 0.1 mmol, 0.1M anhydrous dichloromethane). While stirring at room temperature 2,4 diflurobenzoyl chloride (15 uL, 0.12 mmol) was added followed by triethylamine (20 uL, 0.15 mmol). Once the reaction was complete (determined by LCMS, it was quenched upon the addition of methanol. The solution was then concentrated and purified using a Teledyne ISCO using a reverse phase C18 column, water with 0.1% formic acid/acetonitrile gradient. This afforded the desired product, 8.8 mg. 1H-NMR (CD3OD) d 8.38 (s, 1H), 7.77 (m, 1H), 7.51 (d, 1H), 7.22 (d, 1H), 7.09 (m, 2H), 4.24 (s, 2H), 4.08 (t, 2H), 3.48 (s, 3H), 3.20 (t, 2H). Calculated mass for Chemical Formula: $C_{18}H_{16}F_2N_2O_3$ 346.11, observed 347.1 (M+1, MM API/ESI).

Example 14

1-(6-((1H-benzo[d]imidazol-2-yl)amino)indolin-1-yl)-2-methoxyethan-1-one

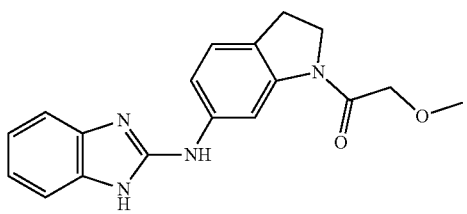 [SMILES: COCC(=O)N1CCc2ccc(Nc3nc4ccccc4[nH]3)cc21]

The title compound was prepared in a similar manner as 1-(6-(benzo[d]oxazol-2-ylamino)indolin-1-yl)-2-methoxyethan-1-one using 2-chlorobenzimidazole. 1H-NMR (CD3OD) d 7.33-7.23 (m, 4H), 7.11 (dd, 1H), 7.03 (s, 1H), 4.24 (s, 2H), 4.10 (t, 2H), 3.48 (s, 3H), 3.20 (t, 2H). Calculated mass for Chemical Formula: $C_{18}H_{18}N_4O_2$, Exact Mass: 322.14, observed 323.2 (M+1, MM API/ESI).

Example 15

3,4-difluoro-N-(1-(2-methoxyacetyl)indolin-6-yl)benzamide

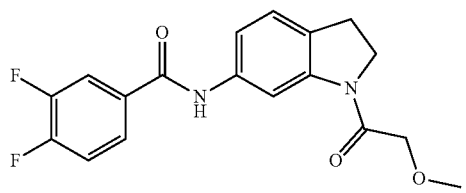 [SMILES: COCC(=O)N1CCc2ccc(NC(=O)c3ccc(F)c(F)c3)cc21]

The title compound was prepared in a similar manner as 2,4-difluoro-N-(1-(2-methoxyacetyl)indolin-6-yl)benzamide. 1H-NMR (CD3OD) d 8.39 (s, 1H), 7.88 (dd, 1H), 7.78 (m, 1H), 7.48 (d, 1H), 7.39 (dd, 1H), 7.21 (d, 1H), 4.24 (s, 2H), 4.08 (t, 2H), 3.48 (s, 3H), 3.19 (t, 2H). Calculated mass for Chemical Formula: $C_{18}H_{16}F_2N_2O_3$ Exact Mass: 346.11, observed 347.1 (M+1, MM API/ESI).

Example 16

2,4,6-trifluoro-N-(1-(2-methoxyacetyl)indolin-6-yl)-N-methylbenzamide

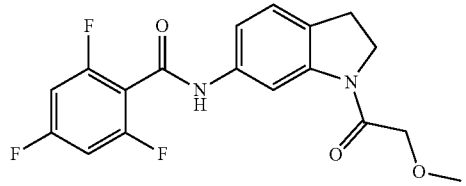 [SMILES: COCC(=O)N1CCc2ccc(NC(=O)c3c(F)cc(F)cc3F)cc21]

The title compound was prepared in a similar manner as 2,4-difluoro-N-(1-(2-methoxyacetyl)indolin-6-yl)benzamide. 1H-NMR (CD3OD) d 8.36 (s, 1H), 7.54 (d, 1H), 7.24 (d, 1H), 7.01 (m, 2H), 4.24 (s, 2H), 4.10 (t, 2H), 3.48 (s, 3H), 3.21 (t, 2H). Calculated mass for Chemical Formula: $C_{19}H_{17}F_3N_2O_3$ Exact Mass: 378.12, observed 379.2 (M+1, MM API/ESI).

Example 17

3,5-difluoro-N-(1-(2-methoxyacetyl)indolin-6-yl)benzamide

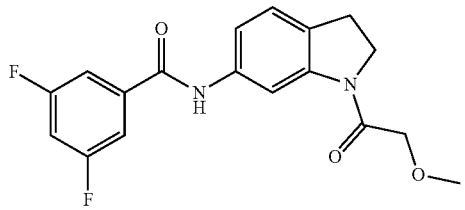 [SMILES: COCC(=O)N1CCc2ccc(NC(=O)c3cc(F)cc(F)c3)cc21]

The title compound was prepared in a similar manner as 2,4-difluoro-N-(1-(2-methoxyacetyl)indolin-6-yl)benzamide. 1H-NMR (CD3OD) d 8.41 (s, 1H), 7.57-7.48 (m, 3H), 7.21 (m, 2H), 4.24 (s, 2H), 4.08 (t, 2H), 3.48 (s, 3H), 3.20 (t, 2H). Calculated mass for Chemical Formula: $C_{18}H_{16}F_2N_2O_3$ 346.11, observed 347.1 (M+1, MM API/ESI).

Example 18

N-(1-(2-methoxyacetyl)indolin-6-yl)benzenesulfonamide

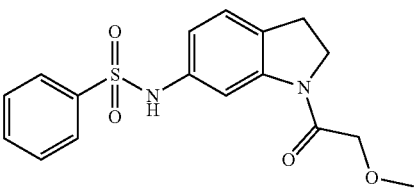 [SMILES: COCC(=O)N1CCc2ccc(NS(=O)(=O)c3ccccc3)cc21]

The title compound was prepared in a similar manner as 2,4-difluoro-N-(1-(2-methoxyacetyl)indolin-6-yl)benzamide. 1H-NMR (CDCl3) d 9.3 (s, NH) 8.08 (s, 1H), 7.98-7.87 (m, 3H), 7.58-7.49 (m, 3H), 7.22 (m, 1H), 4.18 (s, 2H), 4.09 (t, 2H), 3.53 (s, 3H), 3.22 (t, 2H). Calculated mass for Chemical Formula: $C_{17}H_{18}N_2O_4S$ Exact Mass: 346.10, observed 347.1 (M+1, ESI).

Example 19

N-(1-(2-methoxyacetyl)indolin-6-yl)-N-(phenylsulfonyl)benzenesulfonamide

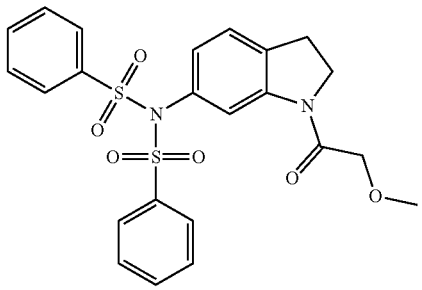 [SMILES: COCC(=O)N1CCc2ccc(N(S(=O)(=O)c3ccccc3)S(=O)(=O)c3ccccc3)cc21]

The title compound was prepared in a similar manner as 2,4-difluoro-N-(1-(2-methoxyacetyl)indolin-6-yl)benzamide. 1H-NMR (CDCl3) d 7.98 (d, 4H), 7.68 (t, 2H), 7.55 (dd, 4H), 7.22 (s, 1H), 7.15 (d, 1H), 6.69 (dd, 1H), 4.11 (m, 4H), 3.49 (s, 3H), 3.24 (t, 2H). Calculated mass for Chemical Formula: $C_{23}H_{22}N_2O_6S_2$ Exact Mass: 486.09, observed 487.1 (M+1, ESI).

Example 20

3-bromo-N-(1-(2-methoxyacetyl)indolin-6-yl)benzamide

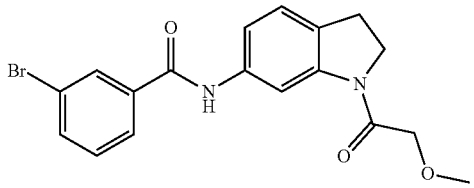 [SMILES: COCC(=O)N1CCc2ccc(NC(=O)c3cccc(Br)c3)cc21]

The title compound was prepared in a similar manner as 2,4-difluoro-N-(1-(2-methoxyacetyl)indolin-6-yl)benzamide. 1H-NMR (CD3OD) d 8.42, (s, 1H), 8.10 (s, 1H), 7.90 (d, 1H), 7.73 (d, 1H), 7.50 (d, 1H), 7.44 (dd, 1H), 7.23 (d 1H), 4.25 (s, 2H), 4.10 (t, 2H), 3.49 (s, 3H), 3.21 (t, 2H). Calculated mass for Chemical Formula: $C_{18}H_{17}BrN_2O_3$, 388.04, observed 389.1 (M+1, MM API/ESI).

Example 21

In Vitro Studies

Renal proximal tubules were isolated from kidneys of female New Zealand white rabbits (1.5-2 kg) using an iron oxide perfusion method and cultured under improved conditions, resulting in normal aerobic metabolism comparable to that found in vivo (Nowak and Schnellmann, 1995). A high-throughput screening assay identified compounds that exhibited elevated FCCP-induced uncoupled oxygen consumption rates (OCRs), indicative of increased mitochondrial capacity (Beeson et al., 2010). OCRs were measured using a Seahorse Bioscience analyzer (North Billerica, Mass.) before (basal) and after addition of 1 mM FCCP, an ionophore that uncouples electron transport from ATP generation. The selective 5-$HT_{1F}$ receptor agonists LY334370 (4-fluoro-N-[3-(1-methyl-4-piperidinyl)-1H-indol-5-yl]benzamide) and LY344864 (N-[(3R)-3-(dimethylamino)-2,3,4,9-tetrahydro-1H-carbazol-6-yl]-4-fluorobenzamide), and the nonselective 5-HT receptor agonist a-methyl 5-HT were purchased from Tocris (Ellisville, Mo.).

For 5-$HT_{1F}$ receptor knockdown, RPTC were treated with scram-bled small interfering RNA (siRNA) (siGENOME nontargeting siRNA #5; Dharmacon RNAi Technologies, Lafayette, Colo.) or siRNA designed against the 5-$HT_{1F}$ receptor using RNAiFect transfection reagent (Qiagen, Valencia, Calif.). siRNA knockdown was accomplished using a 1:1 mixture of siRNA recognizing the following sequences: siRNA-1, 59-CCT TCA GCA TTG TGT ATA T-39 and siRNA-2, 59-CCA CAT TGT TTC CAC TAT T-39. Following a 72-hour exposure, cells were scraped and analyzed for changes in protein levels.

Example 22

In Vivo Studies

Nonfasted naïve 8- to 10-week-old male C57BL/6NCr mice (National Cancer Institute, Frederick, Md.) weighing 25-30 g received an intraperitoneal injection of 250 ml of vehicle (0.9% saline) or test compound every 8 hours for a total of three doses in a 24-hour period (1 mg/kg 3) or one dose of test compound (2 or 10 mg/kg). At the time of euthanasia, organs were harvested, snap-frozen in liquid nitrogen, and stored at 280° C. For the I/R model of acute kidney injury (AKI), mice were subjected to bilateral renal pedicle ligation as described previously (Zhuang et al., 2009; Jesinkey et al., 2014). In brief, renal artery and vein were isolated and blood flow was occluded with a vascular clamp for 18 minutes. Mice were maintained at 37° C. throughout the procedure using a homeothermic heating system. Sham surgery mice received all manipulations with the exception of clamping of the renal pedicles. Mice were treated once daily beginning at 24 hours after reperfusion with saline vehicle or LY344864 (2 mg/kg). (8) Blood was collected from mice via retro-orbital bleed at 24 and 144 hours after surgery. Blood urea nitrogen (BUN) levels were measured using a QuantiChrom Urea Assay Kit (BioAssay Systems, Hayward, Calif.) according to the manufacturer's protocol. Mice were euthanized at 144 hours after the procedure, at which time kidneys were harvested for molecular analyses. Animal protocol was approved by and procedures completed in compliance with Institutional Use and Care of Animals Committee guidelines.

Nucleic Acid Isolation and Quantitative Polymerase Chain Reaction. RPTC were scraped in TRIzol (Life Technologies, Grand Island, N.Y.), and RNA was isolated using a phenol-based centrifugation method. DNA was isolated using a DNeasy Blood and Tissue Kit (Qiagen). cDNA was reverse transcribed from 2 mg RNA using a RevertAid First Strand cDNA Synthesis kit (Thermo Fisher Scientific, Waltham, Mass.), diluted 1:5, and 5 ml added to a real-time Maxima SYBR green quantitative polymerase chain reaction master mix containing 6-carboxy-X-rhodamine (Thermo Fisher Scientific). The following primers were used: actin forward 59-GGG ATG TTT GCT CCA ACC AA-39, actin reverse 59-GCG CTT TTG ACT CAA GGA TTT AA-39; apolipoprotein B (ApoB) forward 59-CGT GGG CTC CAG CAT TCT-39, ApoB reverse 59-TCA CCA GTC ATT TCT GCC TTT G-39; ATP synthase b forward 59-GAG ACC AAG AAG GTC AAG ATG-39, ATP synthase b reverse 59-GAA GGG ATT CGG CCC AAT AAT GCA G 39; cytochrome c oxidase 1 (Cox1) forward 59-TAA TGT AAT CGT CAC CGC ACA-39, Cox1 reverse 59-ATG TGA GGA GCC CCA ATT ATC-39; D loop forward 59-CC- CAAG CAT ATA AGC TAG TA-39, D loop reverse 59-ATA TAA GTC ATA TTT TGG GAA CTA C-39; NDUFB8 forward 59-ACC CAA TCC AAC CGC CTT CA-39, NDUFB8 reverse 59-CTA GGA CCC CAG AGG AAC GC 39; PGC1a forward 59-AGG AAA TCC GAG CTG AGC TGA ACA-39, and PGC1a reverse 59-GCA AGA AGG CGA CAC ATC GAA CAA-39. Changes in gene expression were calculated based on the d-d threshold cycle method. Mitochondrial DNA (mtDNA) copy number was calculated based on comparison of mitochondrial D loop to nuclear ApoB.

Protein Isolation and Western Blotting.

Freshly isolated renal proximal tubules or RPTC (cultured until confluent, about 6 days) were rinsed with ice-cold phosphate-buffered saline, pelleted, and subjected to membrane fractionation (Subcellular Protein Fractionation Kit; Pierce Biotechnology, Rockford, Ill.). For nonfractionated samples, RPTC were scraped in radioimmunoprecipitation assay buffer containing protease inhibitors and phosphatase inhibitors (Sigma-Aldrich, St. Louis, Mo.). Following sonication, protein was quantified using a bicinchoninic acid assay, subjected to SDS-PAGE, transferred onto nitrocellulose membranes, and incubated with primary and secondary antibodies [glyceraldehyde-3-phosphate dehydrogenase from Fitzgerald (Acton, Mass.); Cox1 and NDUFB8 from Invitrogen (Frederick, Md.); kidney injury molecule 1 (KIM-1) from R&D Systems Inc. (Minneapolis, Minn.); ATP synthase b, $5\text{-HT}_{1F}$ receptor, and rabbit and mouse secondary antibodies from Abcam (Cambridge, Mass.)]. Images were acquired with AlphaEase software (Protein Simple, Santa Clara, Calif.) and processed using ImageJ (NIH, Bethesda, Md.) software.

Statistics.

One-way analysis of variance (ANOVA) or Student's t test was used, as appropriate, to analyze data for significance (P, 0.05). Significance in ANOVA was scrutinized for multiple comparisons using the Fisher least significant difference post-hoc test. When normality failed, a one-way ANOVA on Rank-sum was performed.

Example 23

In-Vitro Mitochondrial Biogenesis Dose Responses

In-vitro mitochondrial biogenesis dose responses (reported as EC50 values) were determined from a modification of the assay described in Example 21. Renal proximal tubules were isolated from kidneys of female New Zealand white rabbits and cultured under improved conditions, resulting in normal aerobic metabolism comparable to that found in vivo (Nowak and Schnellmann, 1995). Compounds were incubated at different doses with renal cells for 24 h after which their basal respiration and elevated FCCP-induced uncoupled oxygen consumption rates (OCRs) were measured using a Seahorse Bioscience analyzer (Beeson et al., 2010). Uncoupled OCRs were normalized to vehicle control OCRs and the rates that decrease at high concentrations of drug were eliminated. The remaining dose-dependent responses were fit to a standard Hill equation using non-linear regression to obtain the EC50 values for replicates of N=4-6 where N is the number of individual rabbit renal cell isolations tested for each compound. Results on representative compounds of the invention are shown in the table below:

| Example | EC50 |
|---|---|
| 1 | 20 pM |
| 2 | 20 pM |
| 3 | 20 nM |
| 4 | 2.0 nM |
| 5 | 1.0 nM |
| 6 | 2.0 nM |
| 7 | 0.2 nM |
| 8 | 0.2 nM |
| 9 | 0.2 nM |
| 10 | 0.2 nM |
| 11 | 2.0 nM |
| 12 | 2.0 nM |
| 13 | 20 pM |
| 14 | 20 pM |
| 15 | 0.2 nM |
| 16 | 2.0 pM |
| 17 | 20 pM |
| 18 | NA |
| 19 | 2.0 nM |
| 20 | 20 pM |

Example 24

2,4,6-Trifluoro-N-(6-(1-Methylpiperidine-4-Carbonyl)Pyridin-2-yl)Benzamide 2,4,6-trifluoro-N-(6-(1-methylpiperidine-4-carbonyl)pyridin-2-yl)benzamide was made from a process disclosed in U.S. Pat. No. 7,423,050. The compound was tested by the protocol in Example 23 above and found to have an EC50 value of 0.6 nM.

Example 25

N-(1-(dimethylglycyl)indolin-6-yl)benzenesulfonamide

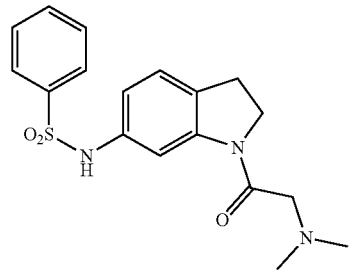 [SMILES: CN(C)CC(=O)N1CCc2ccc(NS(=O)(=O)c3ccccc3)cc21]

To an oven dried flask equipped with a stir bar cooled under an inert atmosphere was added 1-(6-aminoindolin-1-yl)-2-(dimethylamino)ethan-1-one (0.8 mmol, 0.2M in anhydrous chloroform). While stirring at room temperature triethylamine (0.44 mL, 3.2 mmol) was added followed by phenylsulfonylchloride (310 □L, 2.4 mmol). The reaction stirred at room temperature overnight. The next day the reaction was diluted with methanol, filtered and concentrated. Purification was done using a Teledyne ISCO C18 reverse phase column using a gradient of water with 0.1% formic acid/acetonitrile (90:10), to 100% acetonitrile. This afforded the desired product, 11.1 mg. 1H-NMR (CD3OD) d 8.05, (s, 1NH), 7.82-7.77 (m, 3H), 7.55 (m, 1H), 7.47-7.41 (m, 3H), 7.08 (d, 1H), 6.79 (d, 1H), 4.26 (s, 2H), 4.01 (t, 2H), 3.35 (s, 3H), 3.14 (d, 2H), 3.00 (s, 3H). Calculated mass for $C_{18}H_{21}N_3O_3S$, 359.13, observed mass, 360.1 (M+1, MM).

Example 26

N-(1-(diethylglycyl)indolin-6-yl)benzamide

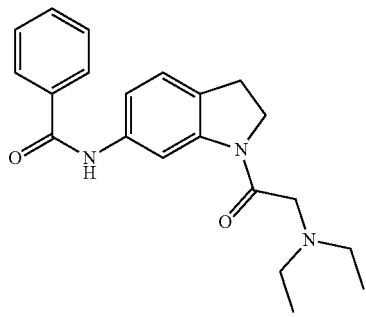 [SMILES: CCN(CC)CC(=O)N1CCc2ccc(NC(=O)c3ccccc3)cc21]

N-(1-(diethylglycyl)indolin-6-yl)benzamide was made in a similar manner to N-(1-(dimethylglycyl)indolin-6-yl)benzenesulfonamide using diethyl amine and benzoyl chloride. 1H-NMR (CD3OD) d 8.59 (s, 1NH), 7.93 (bs, 2H), 7.57-7.51 (m, 3H), 7.38 (bs, 1H), 7.27 (m, 1H), 4.26 (s, 2H), 4.15 (bs, 2H), 3.35-3.24 (m, 6H), 1.38 (bs, 6H). Calculated mass for $C_{21}H_{25}N_3O_2$, 351.19, observed mass, 352.2 (M+1, MM).

Example 27

N-(1-(2-morpholinoacetyl)indolin-6-yl)benzamide

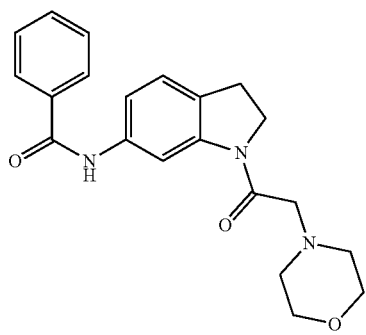 [SMILES: O=C(Nc1ccc2c(c1)N(C(=O)CN1CCOCC1)CC2)c1ccccc1]

N-(1-(2-morpholinoacetyl)indolin-6-yl)benzamide was made in a similar manner to N-(1-(dimethylglycyl)indolin-6-yl)benzenesulfonamide using morpholine and benzoyl chloride. 1H-NMR (CD3OD) d 8.49 (s, 1H), 7.91 (d, 2H), 7.59-7.49 (m, 3H), 7.41 (d, 1H), 7.22 (d, 1H), 4.16 (bs, 2H), 3.82 (bs, 4H), 3.68 (s, 2H), 3.19 (bs, 2H), 2.91 (bs, 4H). Calculated mass for $C_{21}H_{23}N_3O_3$, 365.17, observed mass, 366.2 (M+1, MM).

Example 28

N-(1-(2-(4-methylpiperazin-1-yl)acetyl)indolin-6-yl)benzamide

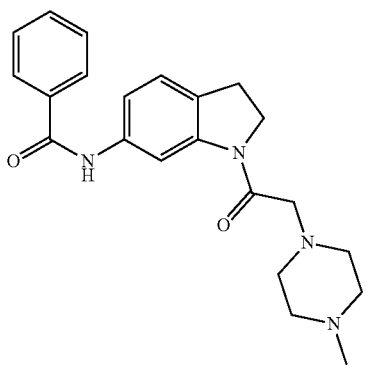 [SMILES: CN1CCN(CC(=O)N2CCc3ccc(NC(=O)c4ccccc4)cc32)CC1]

N-(1-(2-(4-methylpiperazin-1-yl)acetyl)indolin-6-yl)benzamide was made in a similar manner to N-(1-(dimethylglycyl)indolin-6-yl)benzenesulfonamide using N-methyl piperazine and benzoyl chloride. 1H-NMR (CD3OD) d 8.51 (bs, 1H), 7.92 (m, 3H), 7.52 (m, 3H), 7.24 (m, 1H), 4.19 (bs, 2H), 3.52 (bs, 2H), 3.35-2.81 (m, 13H). Calculated mass for $C_{22}H_{26}N_4O_2$, 378.21, observed mass, 379.2 (M+1, MM).

Example 29

Podocytes are known to express the 5-HT$_{1F}$ receptor at similar levels to renal proximal tubule cells and these can also be used to demonstrate 5-HT$_{1F}$ agonist-induced mitochondrial biogenesis. Fully differentiated podocytes were assayed using increased mitochondrial reserve capacity (measured as FCCP-uncoupled oxygen consumption rate) as a measure of mitochondrial biogenesis. Cross validation uses known markers for MB such as NDUFB8, ATP synthase β, Cox1, as has been demonstrated above. As shown in the table below, four representative compounds of the invention demonstrated mitochondrial biogenesis with EC$_{50}$ values ranging from 0.2 nM to 20 nM:

| Example | EC$_{50}$ (nM) |
|---|---|
| 25 | 0.2 |
| 29 | 0.2 |
| 27 | 20 |
| 26 | 20 |
| 4 | 20 |
| 5 | 100 |
| 24 | 20 |
| 6 | 100 |
| 19 | 20 |

For these studies the 1-1P4G5 podocyte clone developed in the Kopp lab at the NIH were used. (25) These cells expressed a SV40-driven temperature sensitive T antigen that enabled the cells to proliferate in an undifferentiated state at the permissive temperature of 33° C. and then after 5 days of culture at 37° C. the cells are fully differentiated as mature podocytes. The differentiated cells were maintained in Advanced RPMI 1640 with 10% fetal calf serum and then plated at 1.5 million cells/96-well Seahorse plate for 48 h prior to treatment with test compound, vehicle control (VC) or validated 5-HT$_{1F}$ agonists. The plates were then transferred to a Seahorse XF96 Instrument during which basal and FCCP-uncoupled rates were measured (the [FCCP]=1 µM). Drugs were treated at a range of 1 nM, 10 nM, 100 nM, 500 nM, and 1 µM and the uncoupled rates were normalized to vehicle control, <0.2% DMSO in media. The doses responses were fit to a Hill function and the EC$_{50}$ values were calculated from the non-linear regression.

The above biological examples and recent scientific studies demonstrate that small molecule inducers of mitochondrial biogenesis improve the outcomes of both acute and chronic renal diseases. (8, 26-28) In particular, it has been shown that agonists of the 5HT1F receptor that induce mitochondrial biogenesis in the kidney are effective therapeutic agents for renal disease, both acute and chronic. The assays above demonstrate that the representative compounds of the invention induce mitochondrial biogenesis in renal cells, both tubular and glomerular, and that they are effective therapeutics for acute kidney injuries and chronic glomerular diseases.

Example 30

Chronic Kidney Disease Model

Renal dysfunction was modeled in mice using the nephrotoxic serum (NTS) induced model. The classical Adriamycin model for glomerular studies relies critically on dosing profiles, has resistance in some murine species, off-target effects in others, and required days (10 days) instead of hours for observable albuminuria (marker for renal compromise, determined by urine collection) compared to the NTS counterpart. (Mallipattu, S. K.; He, J. C. *Am. J. Physiol. Renal Physiol.* 2016, 311, F46-F51; Pippin, J. W.; Brinkkoetter, P. T.; Cormack-Aboud, F. C.; Durvasula, R. V.; Hauser, P. V.; Kowalewska, J.; Krofft, R. D.; Logar, C. M.; Marshall, C. B.; Ohse, T.; Shankland, S. J. *Am. J. Physiol. Renal Physiol.* 2009, 296, F213-F229). Conversely, the NTS model is quick onset (4 h) and has wide species reproducibility.

In this experiment, induction of the nephrotoxic serum (NTS) model (80 mL injection) for glomerular decline was performed using C57/BL mice (15 mice total). After a period of 4 h post NTS injection, formulated drug (compound of Example 6 (2,4,6-trifluoro-N-(6-(4-methylpiperazine-1-carbonyl)pyridin-2-yl)benzamide) or vehicle control (formulation alone, 5% DMSO, 0.9% saline) was administered to the mice (n=10 per drug treated, n=5 for control). Mice were monitored for up to 8 h for any immediate adverse effects. Monitoring of renal function was done by daily urine collection, which will be analyzed by using an SDS-gel electrophoresis on the sixth day (FIG. 1 shows days 1-6), 2$^{nd}$, 6$^{th}$, and 14$^{th}$ day using albumin creatinine ratios to quantitatively assess the level of proteinuria.

As shown in FIG. 1, the compound of Example 6 (2,4,6-trifluoro-N-(6-(4-methylpiperazine-1-carbonyl)pyridin-2-yl)benzamide) attenuated albuminuria in a murine model of glomelular disease. Urine albumin/creatinine ratios were measured in control (NTS+vehicle) and drug treated mice (NTS+drug (example 6) for pre-injection, day 2, day 6, day 12 and day 14. Drug was administered once per day at 2 mg/kg. Thus, it is expected that the compounds of the invention are useful to treat chronic kidney disease.

The invention will be further described, without limitation, by the following numbered paragraphs:

1. A compound according to formula (I):

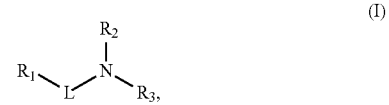

wherein:

L is a bond, —C(O)—, —C(O)CH$_2$ or —S(O)$_2$—;

R$_1$ is an aryl group, a heteroaryl group or an 8- to 10-membered bicyclic heteroaryl group, said aryl, heteroaryl and 8- to 10-membered bicyclic heteroaryl groups optionally mono-, bi- or tri-substituted independently with hydrogen, alkoxy, (=O), —NH-alkoxy, —NH$_2$, —OH, halogen, lower alkyl, —NHC(O)N(CH$_3$)$_2$, —NHS(O)$_2$-phenyl or —NHC(O)-phenyl;

R$_2$ and R$_3$ are, independently of each other, hydrogen, lower alkyl, alkoxy, —NH-lower alkyl, heteroaryl, —S(O)$_2$-phenyl or indolinyl, said heteroaryl and indolinyl groups optionally substituted independently with lower alkyl, C(O)-alkoxy or —C(O)R$_4$, or R$_2$ and R$_3$, together with the nitrogen atom to which they are attached, combine to form a six-membered heterocycloalkyl group optionally substituted with lower alkyl; and R$_4$ is a heterocycloalkyl group optionally substituted with lower alkyl, or a pharmaceutically acceptable salt thereof, with the proviso that said compound is not 2,4,6-trifluoro-N-(6-(1-methylpiperidine-4-carbonyl)pyridin-2-yl)benzamide.

2. The compound according to paragraph 1, wherein R$_1$ is an unsubstituted or substituted aryl group.

3. The compound according to paragraph 1, wherein R$_1$ is an unsubstituted or substituted heteroaryl group.

4. The compound according to paragraph 1, wherein R$_1$ is an unsubstituted or substituted 8- to 10-membered bicyclic heteroaryl group.

5. The compound according to paragraph 1, wherein R$_1$ is unsubstituted phenyl.

6. The compound according to paragraph 1, wherein R$_1$ is phenyl mono-, bi- or tri-substituted independently with halogen or lower alkyl.

7. The compound according to paragraph 1, wherein R$_1$ is pyrido[1,2-a]pyrimidinyl, pyrimidinyl, quinolinyl, benzoimidazolyl or benzooxazolyl, optionally mono-, bi- or tri-substituted independently with hydrogen, alkoxy, (=O), —NH-alkoxy, —NH$_2$, —OH, halogen, lower alkyl, —NHC(O)N(CH$_3$)$_2$, —NHS(O)$_2$-phenyl or —NHC(O)-phenyl.

8. The compound according to paragraph 1, wherein R$_2$ is hydrogen or —S(O)$_2$-phenyl.

9. The compound according to paragraph 1, wherein R$_2$ is hydrogen.

10. The compound according to paragraph 1, wherein and R$_3$ is lower alkyl, alkoxy, —NH-lower alkyl or heteroaryl.

11. The compound according to paragraph 1, wherein R$_3$ is heteroaryl substituted with —C(O)R$_4$.

12. The compound according to paragraph 1, wherein R$_3$ is indolinyl optionally substituted with lower alkyl or C(O)-alkoxy.

13. The compound according to paragraph 1, wherein R$_3$ is indolinyl optionally substituted with
—C(O)-alkoxy.

14. The compound according to paragraph 1, wherein R$_2$ and R$_3$, together with the nitrogen atom to which they are attached, combine to form a six-membered heterocycloalkyl group optionally substituted with lower alkyl.

15. The compound according to paragraph 1, wherein R$_3$ is methoxyethyl, pyridinyl or indolinyl.

16. The compound according to paragraph 1, wherein R$_4$ is piperazinyl or diazepanyl, optionally substituted with lower alkyl.

17. The compound according to paragraph 1, wherein said compound is:
7-methoxy-N-(2-methoxyethyl)-4-oxo-4H-pyrido[1,2-a]pyrimidine-3-carboxamide;
N-(2-methoxyethyl)-7-((2-methoxyethyl)amino)-4-oxo-4H-pyrido[1,2-a]pyrimidine-3-carboxamide;
2-amino-N,1-bis(2-methoxyethyl)-6-oxo-1,6-dihydropyrimidine-5-carboxamide;
4-hydroxy-6,8-dimethoxy-N-(2-methoxyethyl)quinoline-3-carboxamide;
(4-hydroxy-6,8-dimethoxyquinolin-3-yl)(4-methylpiperazin-1-yl)methanone;
2,4,6-trifluoro-N-(6-(4-methylpiperazine-1-carbonyl)pyridin-2-yl)benzamide;
2,4,6-trifluoro-N-(6-(4-methyl-1,4-diazepane-1-carbonyl)pyridin-2-yl)benzamide;
4-methyl-N-(6-(4-methylpiperazine-1-carbonyl)pyridin-2-yl)benzenesulfonamide;
1,1-dimethyl-3-(6-(4-methylpiperazine-1-carbonyl)pyridin-2-yl)urea;
(6-((1H-benzo[d]imidazol-2-yl)amino)pyridin-2-yl)(4-methylpiperazin-1-yl)methanone;
N-(6-(4-methylpiperazine-1-carbonyl)pyridin-2-yl)benzamide;
1-(6-(benzo[d]oxazol-2-ylamino)indolin-1-yl)-2-methoxyethan-1-one;
2,4-difluoro-N-(1-(2-methoxyacetyl)indolin-6-yl)benzamide;
1-(6-((1H-benzo[d]imidazol-2-yl)amino)indolin-1-yl)-2-methoxyethan-1-one;
3,4-difluoro-N-(1-(2-methoxyacetyl)indolin-6-yl)benzamide;
2,4,6-trifluoro-N-(1-(2-methoxyacetyl)indolin-6-yl)-N-methylbenzamide;
3,5-difluoro-N-(1-(2-methoxyacetyl)indolin-6-yl)benzamide;
N-(1-(2-methoxyacetyl)indolin-6-yl)benzenesulfonamide;
N-(1-(2-methoxyacetyl)indolin-6-yl)-N-(phenylsulfonyl)benzenesulfonamide,
3-bromo-N-(1-(2-methoxyacetyl)indolin-6-yl)benzamide,
N-(1-(dimethylglycyl)indolin-6-yl)benzenesulfonamide,
N-(1-(diethylglycyl)indolin-6-yl)benzamide,
N-(1-(2-morpholinoacetyl)indolin-6-yl)benzamide or
N-(1-(2-(4-methylpiperazin-1-yl)acetyl)indolin-6-yl)benzamide,
or a pharmaceutically acceptable salt thereof.

18. A pharmaceutical composition, comprising a therapeutically effective amount of a compound according to paragraph 1 or 17, or a pharmaceutically acceptable salt thereof, and a pharmaceutically acceptable carrier.

19. A method for treating acute kidney injury, comprising the step of administering a therapeutically effective amount of a compound according to paragraph 1 or 17, or a pharmaceutically acceptable salt thereof, or a therapeutically effective amount of 2,4,6-trifluoro-N-(6-(1-methylpiperidine-4-carbonyl)pyridin-2-yl)benzamide, or a pharmaceutically acceptable salt thereof, and a pharmaceutically acceptable carrier to a patient in need thereof.

20. A method for treating chronic kidney disease, comprising the step of administering a therapeutically effective amount of a compound according to paragraph 1 or 17, or a pharmaceutically acceptable salt thereof, or a therapeutically effective amount of 2,4,6-trifluoro-N-(6-(1-methylpiperidine-4-carbonyl)pyridin-2-yl)benzamide, or a pharmaceutically acceptable salt thereof, and a pharmaceutically acceptable carrier to a patient in need thereof.

21. A method of inducing mitochondrial biogenesis in a patient in need thereof, comprising the step of administering a therapeutically effective amount of a compound according to paragraph 1 or 17, or a pharmaceutically acceptable salt thereof, or a therapeutically effective amount of 2,4,6-trifluoro-N-(6-(1-methylpiperidine-4-carbonyl)pyridin-2-yl)benzamide, or a pharmaceutically acceptable salt thereof, and a pharmaceutically acceptable carrier to said patient.

REFERENCES

1. Civitarese, A. E.; Ravussin, E., Minireview: Mitochondrial Energetics and Insulin Resistance. *Endocrinology* 2008, 149 (3), 950-954.
2. Hagen, T. M.; Moreau, R.; Suh, J. H.; Visioli, F., Mitochondrial Decay in the Aging Rat Heart. *Annals of the New York Academy of Sciences* 2002, 959 (1), 491-507.
3. Seo, A. Y.; Joseph, A.-M.; Dutta, D.; Hwang, J. C. Y.; Aris, J. P.; Leeuwenburgh, C.,
New insights into the role of mitochondria in aging: mitochondrial dynamics and more. *Journal of Cell Science* 2010, 123 (15), 2533-2542.
4. Baloyannis, S. J., Mitochondrial alterations in Alzheimer's disease. *Journal of Alzheimer's Disease* 2006, 9 (2), 119-126.
5. Funk, J. A.; Odejinmi, S.; Schnellmann, R. G., SRT1720 induces mitochondrial biogenesis and rescues mitochondrial function after oxidant injury in renal proximal tubule cells. *The Journal of pharmacology and experimental therapeutics* 2010, 333 (2), 593-601.
6. Medeiros, D. M., Assessing mitochondria biogenesis. *Methods* 2008, 46 (4), 288-294.
7. Brooks, C.; Wei, Q.; Cho, S.-G.; Dong, Z., Regulation of mitochondrial dynamics in acute kidney injury in cell culture and rodent models. *The Journal of Clinical Investigation* 2009, 119 (5), 1275-1285.
8. Garrett, S. M.; Whitaker, R. M.; Beeson, C. C.; Schnellmann, R. G. Agonism of the 5-hydroxytryptamine 1F receptor promotes mitochondrial biogenesis and recovery from acute kidney injury. *J Pharmacol Exp Ther.* 2014 350(2), 257-64.
9. Wills, L. P.; Trager, R. E.; Beeson, G. C.; Lindsey, C. C.; Peterson, Y. K.; Beeson, C. C.; Schnellmann, R. G., The beta2-Adrenoceptor Agonist Formoterol Stimulates Mitochondrial Biogenesis. *J Pharmacol Exp Ther* 2012, 342 (1), 106-18.
10. Beeson, C. C.; Beeson, G. C.; Schnellmann, R. G., A high-throughput respirometric assay for mitochondrial biogenesis and toxicity. *Analytical Biochemistry,* 2010, 404 (1), 75-81.
11. Peterson, Y. K.; Cameron, R. B.; Wills, L. P.; Trager, R. E.; Lindsey, C. C.; Beeson, C. C.; Schnellmann, R. G., β2-Adrenoceptor agonists in the regulation of mitochondrial biogenesis. *Bioorganic & Medicinal Chemistry Letters* 2013, 23 (19), 5376-81.

12. Rasbach, K. A.; Funk, J. A.; Jayavelu, T.; Green, P. T.; Schnellmann, R. G., 5-hydroxytryptamine receptor stimulation of mitochondrial biogenesis. *The Journal of pharmacology and experimental therapeutics* 2010, 332 (2), 632-9.
13. Xu, J.; Yao, B.; Fan, X.; Langworthy, M. M.; Zhang, M.-Z.; Harris, R. C., Characterization of a putative intrarenal serotonergic system. *American journal of physiology. Renal physiology* 2007, 293 (5), F1468-75.
14. Nebigil, C. G.; Maroteaux, L., Functional consequence of serotonin/5-HT2B receptor signaling in heart: role of mitochondria in transition between hypertrophy and heart failure?*Circulation* 2003, 108 (7), 902-8.
15. Nowak, G.; Schnellmann, R. G., Improved culture conditions stimulate gluconeogenesis in primary cultures of renal proximal tubule cells. *The American journal of physiology* 1995, 268 (4 Pt 1), C1053-61.
16. Nowak, G.; Schnellmann, R. G., L-ascorbic acid regulates growth and metabolism of renal cells: improvements in cell culture. *Am J Physiol Cell Physiol* 1996, 271 (6), C2072-2080.
17. *Molecular Operating Environment (MOE)*, 2013.08; 2013.
18. Irwin, J. J.; Shoichet, B. K., ZINC—a free database of commercially available compounds for virtual screening. *J Chem Inf Model* 2005, 45 (1), 177-82.
19. Wang, C.; Jiang, Y.; Ma, J.; Wu, H.; Wacker, D.; Katritch, V.; Han, G. W.; Liu, W.; Huang, X.-P.; Vardy, E.; McCorvy, J. D.; Gao, X.; Zhou, X. E.; Melcher, K.; Zhang, C.; Bai, F.; Yang, H.; Yang, L.; Jiang, H.; Roth, B. L.; Cherezov, V.; Stevens, R. C.; Xu, H. E., Structural Basis for Molecular Recognition at Serotonin Receptors. *Science* 2013, 340 (6132), 610-614.
20. Goldstein, D. J.; Roon, K. I.; Offen, W. W.; Ramadan, N. M.; Phebus, L. A.; Johnson, K. W.; Schaus, J. M.; Ferrari, M. D., Selective seratonin 1F (5-HT(1F)) receptor agonist LY334370 for acute migraine: a randomised controlled trial. *Lancet* 2001, 358 (9289), 1230-4.
21. Agosti, R. M., 5HT1F- and 5HT7-receptor agonists for the treatment of migraines. *CNS & neurological disorders drug targets* 2007, 6 (4), 235-7.
22. Ramadan, N. M.; Skljarevski, V.; Phebus, L. A.; Johnson, K. W., 5-HT1F receptor agonists in acute migraine treatment: a hypothesis. *Cephalalgia: an international journal of headache* 2003, 23 (8), 776-85.
23. Wainscott, D. B.; Krushinski, J. H.; Audia, J. E.; Schaus, J. M.; Zgombick, J. M.; Lucaites, V. L.; Nelson, D. L., [3H]LY334370, a novel radioligand for the 5-HT1F receptor. I. In vitro characterization of binding properties. *Naunyn-Schmiedeberg's archives of pharmacology* 2005, 371 (3), 169-77.
24. Phebus, L. A.; Johnson, K. W.; Zgombick, J. M.; Gilbert, P. J.; Van Belle, K.; Mancuso, V.; Nelson, D. L. G.; Calligaro, D. O.; Kiefer Jr, A. D.; Branchek, T. A.; Flaugh, M. E., Characterization of LY344864 as a pharmacological tool to study 5-HT1F receptors: Binding affinities, brain penetration and activity in the neurogenic dural inflammation model of migraine. *Life Sciences* 1997, 61 (21), 2117-2126.
25. Abe, Y.; Sakairi, T.; Kajiyama, H.; Shrivastav, S.; Beeson, C.; Kopp, J. B. Bioenergetic characterization of mouse podocytes. *Am. J. Cell Physiol.* 2010, 299, C464-C476.
26. Gibbs, W. S.; Garrett, S. M.; Beeson, C. C.; Schnellmann, R. G. Identification of Dual Mechanisms Mediating 5-hydroxytryptamine Receptor 1F Induced Mitochondrial Biogenesis. *Am J Physiol Renal Physiol.* 2017 Oct. 18:ajprenal.00324.2017. doi: 10.1152/ajprenal.00324.2017.
27. Cameron, R. B.; Beeson, C. C.; Schnellmann, R. G. Development of Therapeutics That Induce Mitochondrial Biogenesis for the Treatment of Acute and Chronic Degenerative Diseases. *J. Med. Chem.* 2016 59(23), 10411-10434.
28. Whitaker, R. M.; Corum, D.; Beeson, C. C.; Schnellmann, R. G. Mitochondrial Biogenesis as a Pharmacological Target: A New Approach to Acute and Chronic Diseases. *Annu Rev Pharmacol Toxicol.* 2016, 56, 229-49.

It is to be understood that the invention is not limited to the particular embodiments of the invention described above, as variations of the particular embodiments may be made and still fall within the scope of the appended claims.

What is claimed is:
1. A compound, wherein said compound is:
   7-methoxy-N-(2-methoxyethyl)-4-oxo-4H-pyrido[1,2-a]pyrimidine-3-carboxamide;
   N-(2-methoxyethyl)-7-((2-methoxyethyl)amino)-4-oxo-4H-pyrido[1,2-a]pyrimidine-3-carboxamide;
   2-amino-N,1-bis(2-methoxyethyl)-6-oxo-1,6-dihydropyrimidine-5-carboxamide;
   4-hydroxy-6,8-dimethoxy-N-(2-methoxyethyl)quinoline-3-carboxamide;
   (4-hydroxy-6,8-dimethoxyquinolin-3-yl)(4-methylpiperazin-1-yl)methanone;
   2,4,6-trifluoro-N-(6-(4-methylpiperazine-1-carbonyl)pyridin-2-yl)benzamide;
   2,4,6-trifluoro-N-(6-(4-methyl-1,4-diazepane-1-carbonyl)pyridin-2-yl)benzamide;
   4-methyl-N-(6-(4-methylpiperazine-1-carbonyl)pyridin-2-yl)benzenesulfonamide;
   1,1-dimethyl-3-(6-(4-methylpiperazine-1-carbonyl)pyridin-2-yl)urea;
   (6-((1H-benzo[d]imidazol-2-yl)amino)pyridin-2-yl)(4-methylpiperazin-1-yl)methanone;
   N-(6-(4-methylpiperazine-1-carbonyl)pyridin-2-yl)benzamide;
   1-(6-(benzo[d]oxazol-2-ylamino)indolin-1-yl)-2-methoxyethan-1-one;
   2,4-difluoro-N-(1-(2-methoxyacetyl)indolin-6-yl)benzamide;
   1-(6-((1H-benzo[d]imidazol-2-yl)amino)indolin-1-yl)-2-methoxyethan-1-one;
   3,4-difluoro-N-(1-(2-methoxyacetyl)indolin-6-yl)benzamide;
   2,4,6-trifluoro-N-(1-(2-methoxyacetyl)indolin-6-yl)-N-methylbenzamide;
   3,5-difluoro-N-(1-(2-methoxyacetyl)indolin-6-yl)benzamide;
   N-(1-(2-methoxyacetyl)indolin-6-yl)benzenesulfonamide;
   N-(1-(2-methoxyacetyl)indolin-6-yl)-N-(phenylsulfonyl)benzenesulfonamide,
   3-bromo-N-(1-(2-methoxyacetyl)indolin-6-yl)benzamide,
   N-(1-(dimethylglycyl)indolin-6-yl)benzenesulfonamide,
   N-(1-(diethylglycyl)indolin-6-yl)benzamide,
   N-(1-(2-morpholinoacetyl)indolin-6-yl)benzamide or
   N-(1-(2-(4-methylpiperazin-1-yl)acetyl)indolin-6-yl)benzamide,
   or a pharmaceutically acceptable salt thereof.
2. A pharmaceutical composition, comprising a therapeutically effective amount of a compound according to claim

1, or a pharmaceutically acceptable salt thereof, and a pharmaceutically acceptable carrier.

3. A method for treating acute kidney injury, comprising the step of administering a therapeutically effective amount of a compound according to claim 1, or a pharmaceutically acceptable salt thereof, or a therapeutically effective amount of 2,4,6-trifluoro-N-(6-(1-methylpiperidine-4-carbonyl)pyridin-2-yl)benzamide, or a pharmaceutically acceptable salt thereof, and a pharmaceutically acceptable carrier to a patient in need thereof.

4. A method for treating chronic kidney disease, comprising the step of administering a therapeutically effective amount of a compound according to claim 1, or a pharmaceutically acceptable salt thereof, or a therapeutically effective amount of 2,4,6-trifluoro-N-(6-(1-methylpiperidine-4-carbonyl)pyridin-2-yl)benzamide, or a pharmaceutically acceptable salt thereof, and a pharmaceutically acceptable carrier to a patient in need thereof.

5. A method of inducing mitochondrial biogenesis in a patient in need thereof, comprising the step of administering a therapeutically effective amount of a compound according to claim 1, or a pharmaceutically acceptable salt thereof, or a therapeutically effective amount of 2,4,6-trifluoro-N-(6-(1-methylpiperidine-4-carbonyl)pyridin-2-yl)benzamide, or a pharmaceutically acceptable salt thereof, and a pharmaceutically acceptable carrier to said patient.

* * * * *